United States Patent [19]

George et al.

[11] Patent Number: 5,246,939

[45] Date of Patent: * Sep. 21, 1993

[54] 2-AMINOPYRIMIDINE-4-CARBOXAMIDE DERIVATIVES, THEIR PREPARATION AND THEIR USE IN THERAPEUTICS

[75] Inventors: Pascal George, St. Arnoult en Yvelines; Christian Maloizel, Meudon; Benoit Marabout, Massy; Jean-Pierre Merly, Sceaux, all of France

[73] Assignee: Synthelabo, Le Plessis Robinson, France

[*] Notice: The portion of the term of this patent subsequent to May 11, 2010 has been disclaimed.

[21] Appl. No.: 903,977

[22] Filed: Jun. 26, 1992

[30] Foreign Application Priority Data

Jun. 27, 1991 [FR] France ............................ 91 07938
May 18, 1992 [FR] France ............................ 92 06005

[51] Int. Cl.$^5$ .................. A61K 31/505; C07D 239/32
[52] U.S. Cl. .................... 514/275; 544/332; 544/333
[58] Field of Search ................. 544/332, 333; 514/275

[56] References Cited

U.S. PATENT DOCUMENTS 4,853,387 8/1989 Manoury et al. ............... 514/272

FOREIGN PATENT DOCUMENTS 0480794 4/1992 European Pat. Off. .

OTHER PUBLICATIONS

Chemical Abstracts, No. 70, 1969, Abst. No. 76976P.

Primary Examiner—Mukund J. Shah
Assistant Examiner—Y. N. Gupta
Attorney, Agent, or Firm—Jacobson, Price, Holman & Stern

[57] ABSTRACT

A compound which is a 2-aminopyrimidine carboxamide derivative represented by formula (I)

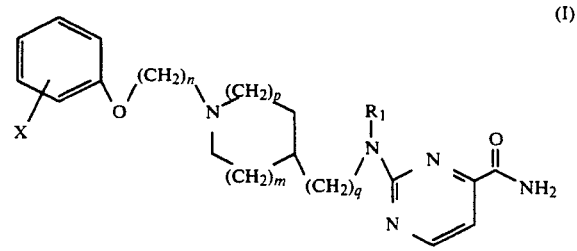

in which

X represents hydrogen, fluorine, chlorine, methyl, 1-methylethyl or methoxy, with the proviso that more than one substituent X may be present in which case each X may be the same or different, n represents 2 or 3, m represents 1, in which case p represents 1, or else m represents 0, in which case p represents 2, q represents 0 or 1, and $R_1$ represents a hydrogen atom;

or a pharmaceutically acceptable acid addition salt thereof.

A compound of formula (I) has $\alpha_1$-adrenergic receptor antagonist activity and is useful as a therapeutic substance.

7 Claims, No Drawings

2-AMINOPYRIMIDINE-4-CARBOXAMIDE DERIVATIVES, THEIR PREPARATION AND THEIR USE IN THERAPEUTICS

The invention relates to 2-aminopyrimidine-4-carboxamide derivatives, their preparation and their use in therapeutics.

SUMMARY OF THE INVENTION

The invention provides a compound which is a 2-aminopyrimidine carboxamide derivative represented by formula (I)

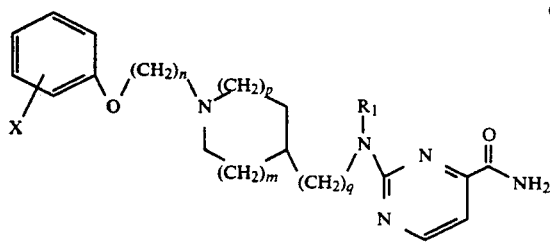

in which

X represents a substituent selected from the group consisting of hydrogen, fluorine, chlorine, methyl, 1-methylethyl and methoxy, with the proviso that more than one substituent X may be present in which case each X may be the same or different, n represents 2 or 3, m represents 1, in which case p represents 1, or else m represents 0, in which case p represents 2, q represents 0 or 1, and $R_1$ represents a hydrogen atom;

or a pharmaceutically acceptable acid addition salt thereof.

A compound of the invention may be a pure enantiomer or a mixture of enantiomers, for example racemate.

The invention also provides a process for preparing a compound of formula (I).

DETAILED DESCRIPTION OF THE INVENTION

A compound of the invention preferably has one or two substituents X. When one substituent X is present, the substituent is preferably at the 2- or 4- position. When two substituents X are present the substituents are preferably at the 2- and 5- positions.

In accordance with the invention, the compounds of general formula (I) can be prepared according to one of the two processes illustrated by Schemes 1 and 2 which follow. If desired the compounds of general formula (I) can be converted into acid addition salts in a manner known per se.

Scheme 1

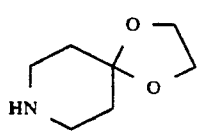

(II')

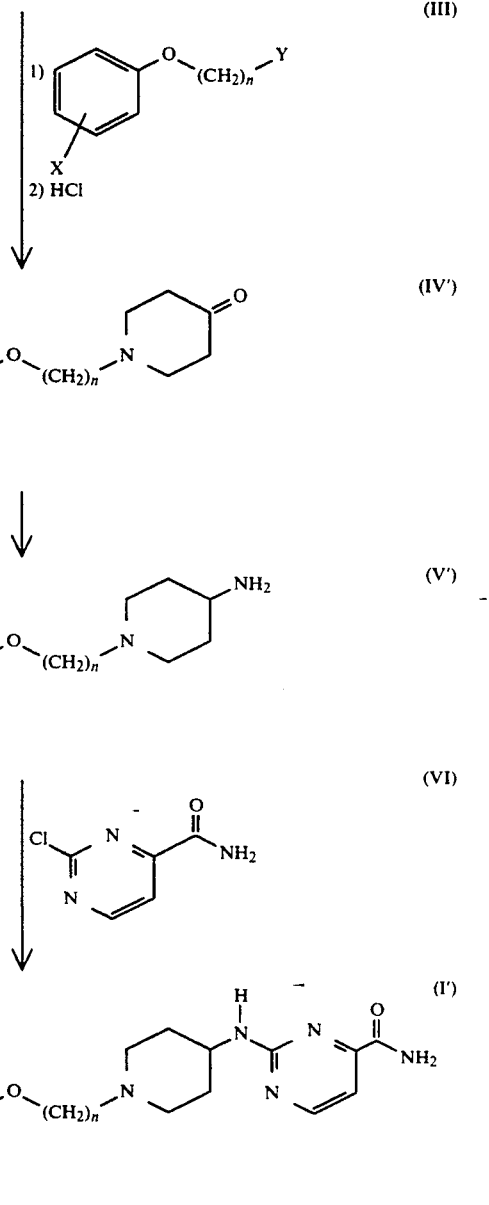

Scheme 1 concerns only the compounds of general formula (I) in which m=p=1 and q=0, which corresponds to the general formula (I').

According to this scheme, the substituted piperidine of formula (II') is reacted with a phenoxyalkyl halide of general formula (III), in which X and n are as defined above and Y represents a chlorine or bromine atom, in 2-butanone in the presence of an inorganic base, for example potassium carbonate, at a temperature of 80° C. The acetal obtained is then converted to a ketone of general formula (IV') by hydrolysis, for example with hydrochloric acid.

When all the substituents X are different from halogen atoms, the ketone of general formula (IV') can be converted to an amine of general formula (V') by reaction with ammonia in an aliphatic alcohol, for example methanol, in the presence of 10% palladium on charcoal under a hydrogen atmosphere.

When one of the substituents X is a halogen atom, the ketone of general formula (IV') can be reacted with methoxyamine in aqueous ethanol and the oxime obtained then reduced by an alkali metal hydride, for example lithium aluminium hydride, in an ether solvent such as tetrahydrofuran, to obtain the amine of general formula (V').

The 2-aminopyrimidine-4-carboxamide of general formula (I') is obtained by reacting the amine of formula (V') with 2-chloropyrimidine-4-carboxamide of formula (VI), in an aprotic solvent, for example N,N-dimethylformamide, in the presence of an inorganic base, for example potassium carbonate, at a temperature of 20° to 40° C.

The substituted piperidine of formula (II'), or 1,4-dioxa-8-azaspiro[4.5]decane, is commercially available.

The phenoxyalkyl halides of general formula (III) can be prepared by methods analogous to those described in J. Pharm. Sci., 1984, 73/9, 1241–1244, or in Synthesis 1990, 1069–1071.

The 2-chloropyrimidine-4-carboxamide of formula (VI) can be prepared from 2-chloropyrimidine-4-carbonitrile by treatment with gaseous hydrochloric acid in formic acid, the said nitrile being itself prepared according to the method described in J. Het. Chem. 1964, 1, 130–133.

According to Scheme 2 below, an amine of general formula (II), in which m, p, q and $R_1$ are as defined above and R represents an amine-protecting group, for example a benzyloxycarbonyl or tert-butoxycarbonyl group, is first reacted with a phenoxyalkyl halide of general formula (III), in which X and n are as defined above and Y represents a chlorine or bromine atom, in an aprotic solvent, for example N,N-dimethylformamide, in the presence of a base, for example an inorganic base such as potassium carbonate, at a temperature of 40° to 100° C.

A diamine of general formula (IV) is obtained, which is then deprotected, according to the nature of the protecting group R, by a method analogous to those described in the literature, for example by hydrogenation in the presence of palladium on charcoal (in the case of a benzyloxycarbonyl group) or by reaction with trifluoroacetic acid in dichloromethane (in the case of a tert-butoxycarbonyl group).

A diamine of general formula (V) is obtained, which is finally reacted with 2-chloropyrimidine-4-carboxamide of formula (VI) in an aprotic solvent, for example N,N-dimethylformamide, in the presence of a base, for example an inorganic base such as potassium carbonate, at a temperature of 20° to 60° C.

The protected diamines of general formula (II), in which q represents the number 1, can be prepared by a method analogous to those described for the synthesis of tert-butyl piperidine-4-carbamate (q=0) in patent applications DE-2831431, EP-410278 and EP-417698.

The phenoxyalkyl halides of general formula (III) and 2-chloropyrimidine-4-carboxamide of formula (VI) can be prepared as described in connection with Scheme 1.

Scheme 2

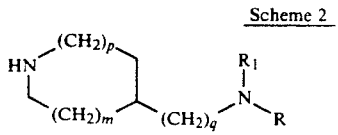

(II)

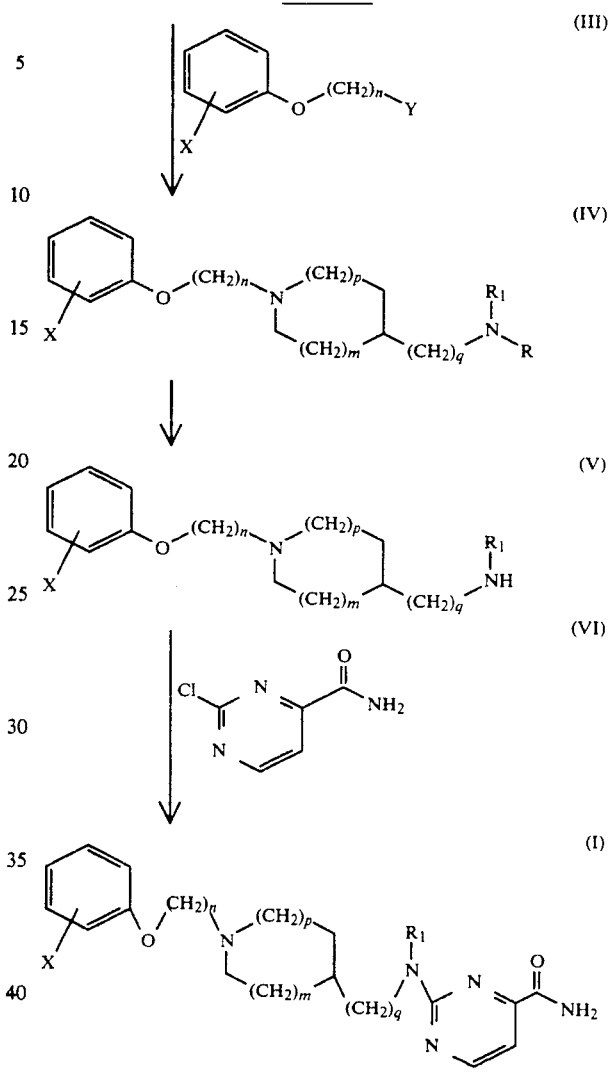

The following examples illustrate in detail the preparation of some compounds in accordance with the invention. Elemental microanalyses and IR and NMR spectra confirm the structures of the products obtained. The numbers between parentheses in the headings correspond to those in the table given later.

EXAMPLE 1

Compound No. 1

2-[1-[2-(2-Methoxyphenoxy)ethyl]piperidin-4-ylamino]pyrimidine-4-carboxamide, hydrochloride.

1.1. 8-[2-(2-Methoxyphenoxy)ethyl]-1,4-dioxa-8-azaspiro-[4.5]decane.

32.2 g (0.139 mol) of 2-(2-methoxyphenoxy)ethyl bromide, 19.95 g (0.139 mol) of 1,4-dioxa-8-azaspiro[4.5]-decane, 28.8 g (0.208 mol) of potassium carbonate and 322 ml of 2-butanone are introduced into a 1 liter round bottom flask. The mixture is heated and stirred at the reflux temperature of the solvent for 7 hours. The mixture is cooled, the insoluble material is removed by filtration and the filtrate is concentrated under reduced pressure to give 40.8 g of oil.

1.2 1-[2-(2-Methoxyphenoxy)ethyl]piperidin-4-one.

40.8 g (0.139 mol) of 8-[2-(2-methoxyphenoxy)ethyl]-1,4-dioxa-8-azaspiro[4.5]decane are dissolved in 408 ml of acetic acid and 40.8 ml of concentrated hydrochloric acid. The mixture is brought to reflux temperature for 30 minutes. The mixture is concentrated under reduced pressure and the residue is then taken up with a little water and dichloromethane. The solution is alkalified with concentrated aqueous ammonia, extracted with dichloromethane, the organic phase is then dried over magnesium sulphate and the solvent evaporated under reduced pressure. The solid obtained is recrystallised from 2-propanol to give 25.4 g of product.

Melting point: 73°-75° C.

1.3. 1-[2-(2-Methoxyphenoxy)ethyl]piperidin-4-amine, hydrochloride.

5.4 g (0.0216 mol) of 1-[2-(2-methoxyphenoxy)ethyl]piperidin-4-one and 200 ml of methanol are introduced into a 500 ml flask of a Parr apparatus. The mixture is cooled in an ice bath, the solution is saturated with ammonia and 0.5 g of 10% palladium on charcoal is then added.

The mixture is stirred for 5 hours under a hydrogen atmosphere at ambient pressure, is then filtered and concentrated under reduced pressure.

The hydrochloride of the compound is prepared, which is recrystallised from a 2-propanol/ethyl acetate mixture. 2.2 g of compound are obtained.

Melting point: 128°-131° C.

1.4. 2-[1-[2-(2-Methoxyphenoxy)ethyl]piperidin-4-ylamino]pyrimidine-4-carboxamide, hydrochloride.

2.1 g (0.0073 mol) of 1-[2-(2-methoxyphenoxy)ethyl]piperidin-4-amine, 1.15 g (0.0073 mol) of 2-chloropyrimidine-4-carboxamide and 3 g (0.0219 mol) of potassium carbonate in solution in 42 ml of N,N-dimethylformamide are introduced into a 100 ml round bottom flask.

The mixture is stirred for 48 hours at room temperature, it is poured into water and then extracted three times with ethyl acetate. The organic phase is washed once with water, dried over sodium sulphate, filtered and the filtrate is concentrated under reduced pressure. The base is recrystallised from 2-propanol to give 0.7 g of base.

19 ml of a 0.1N hydrochloric acid solution in 2-propanol are added to the base in solution in a mixture of dichloromethane and 2-propanol. The solvent is evaporated under reduced pressure and the hydrochloride is recrystallised from 2-propanol. 0.26 g of compound are obtained.

Melting point: 194°-196° C.

EXAMPLE 2

Compound No. 2

2-[1-[2-(4-Fluorophenoxy)ethyl]piperidin-4-ylamino]pyrimidine-4-carboxamide, hydrochloride.

2.1 8-[2-(4-Fluorophenoxy)ethyl]-1,4-dioxa-8-azaspiro-[4.5]decane.

21.91 g (0.1 mol) of 2-(4-fluorophenoxy)ethyl bromide, 14.32 g (0.1 mol) of 1,4-dioxa-8-azaspiro[4.5]decane and 20.73 g (0.15 mol) of potassium carbonate are introduced into 250 ml of 2-butanone and the mixture is heated at boiling for 7 hours.

The mixture is cooled to room temperature, filtered, the insoluble material washed with 200 ml of ether and the solvents evaporated under reduced pressure. 29 g of a yellow oil are obtained which is used as it is in the following stage.

2.2. 1-[2-(4-Fluorophenoxy)ethyl]piperidin-4-one.

30 ml of concentrated hydrochloric acid are added to a solution of 28.13 g (0.1 mol) of 8-[2-(4-fluorophenoxy)ethyl]-1,4-dioxa-8-azaspiro [4.5]decane in 300 ml of acetic acid. The mixture is heated for 1 hour at boiling, is evaporated under reduced pressure, the residue is treated with 150 ml of 1N sodium hydroxide solution and is extracted with dichloromethane. The organic phase is dried over magnesium sulphate, filtered and the solvent evaporated under reduced pressure. 24.9 g of product are obtained which is used as it is in the following stage.

2.3. 1-[2-(4-Fluorophenoxy)ethyl]piperidin-4-amine.

20.15 g (0.085 mol) of 1-[2-(4-fluorophenoxy)-ethyl]-piperidin-4-one, 10.65 g (0.1275 mol) of methoxyamine hydrochloride and 11.51 g (0.140 mol) of sodium acetate are placed in 300 ml of ethanol and 80 ml of water and the mixture is heated for 2 hours.

The ethanol is evaporated, 100 ml of water are added and the mixture is extracted with dichloromethane. The organic phase is dried over magnesium sulphate, filtered and evaporated under reduced pressure.

4.84 g (0.127 mol) of lithium aluminium hydride are suspended in 150 ml of tetrahydrofuran and then the crude product obtained previously is added dropwise. The mixture is heated at reflux temperature for 18 hours.

The excess hydride is hydrolysed with 5 ml of sodium hydroxide solution, the mixture is filtered on magnesium sulphate and the solvent evaporated under reduced pressure. The residue is taken up with water, 100 ml of 2N sodium hydroxide solution are added and the mixture is extracted with dichloromethane. The organic phase is dried over magnesium sulphate, filtered and the solvent evaporated. The compound is obtained in the base form.

The hydrochloride is prepared by adding a 0.1N hydrochloric acid solution in 800 ml of 2-propanol. 9.93 g of compound are obtained.

Melting point: 159°-162° C.

2.4. 2-[1-[2-(4-Fluorophenoxy)ethyl]piperidin-4-ylamino]-pyrimidine-4-carboxamide, hydrochloride.

5.5 g (0.02 mol) of 1-[2-(4-fluorophenoxy)ethyl]-piperidin-4-amine, 3.15 g (0.02 mol) of 2-chloropyrimidine-4-carboxamide, 6.91 g (0.05 mol) of potassium carbonate and 0.4 g of sodium iodide are suspended, under argon, in 40 ml of N,N-dimethylformamide.

The mixture is stirred at room temperature for 17 hours and then at 40°-45° C. for 8 hours. The mixture is cooled to room temperature, poured into 150 ml of water and extracted with ethyl acetate. The organic phase is washed with water, dried over magnesium sulphate, filtered and the solvent evaporated under reduced pressure. After chromatography on silica (eluent: dichloromethane/methanol 97.5/2.5 to 90/10), 4.95 g of base are obtained.

The hydrochloride is prepared from it by reaction with a 0.1N hydrochloric acid solution in 2-propanol. After recrystallisation from ethanol, 4.1 g of compound are obtained.

Melting point: 202°-205° C.

EXAMPLE 3

Compound No. 8

2-[[[1-[2-(4-Fluorophenoxy)ethyl]piperidin-4-yl]methyl]-amino]pyrimidine-4-carboxamide, fumarate.

3.1. 1,1-Dimethylethyl [[1-[2-(4-fluorophenoxy)ethyl]-piperidin-4-yl]methyl]carbamate.

6.8 g (0.031 mol) of 2-(4-fluorophenoxy)ethyl bromide, 6.0 g (0.028 mol) of 1,1-dimethylethyl [(piperidin-4-yl)methyl]carbamate, 5.8 g of potassium carbonate and 60 ml of N,N-dimethylformamide are introduced into a 250 ml, three-necked round bottom flask and the mixture is heated at between 90° and 100° C. for 8 hours under an argon atmosphere.

The mixture is cooled to room temperature, poured into 250 ml of water and extracted with ethyl acetate. The organic phase is washed with water, dried over magnesium sulphate, filtered and the solvent evaporated under reduced pressure.

After purification by chromatography on a silica gel column (eluent: dichloromethane/methanol 98/2 to 92/8), 9 g of oily product are isolated which is used as it is in the following stage.

3.2. 1-[2-(4-Fluorophenoxy)ethyl]piperidine-4-methenamine. 8.8 g (0.025 mol) of 1,1-dimethylethyl [[1-[2-(4-fluorophenoxy)ethyl]piperidin-4-yl]methyl]-carbamate, 90 ml of dichloromethane and 90 ml of trifluoroacetic acid are introduced into a 500 ml, three-necked round bottom flask and the mixture is heated at 40° C. for 4.5 hours.

The mixture is concentrated under reduced pressure, the crude residue is treated with 200 ml of 1N sodium hydroxide solution and the mixture is extracted with dichloromethane.

The organic phase is washed with water, dried over magnesium sulphate, filtered and the solvent evaporated under reduced pressure.

6.2 g of yellow oil are obtained which is used as it is in the following stage.

3.3. 2-[[[1-[2-(4-Fluorophenoxy)ethyl]piperidin-4-yl]-methyl]amino]pyrimidine-4-carboxamide, fumarate.

A suspension of 3.1 g (0.0123 mol) of 1-[2-(4-fluorophenoxy)ethyl]piperidine-4-methenamine, 2.0 g (0.0127 mol) of 2-chloropyrimidine-4-carboxamide, 2.55 g (0.0185 mol) of potassium carbonate, 0.3 g of sodium iodide and 65 ml of N,N-dimethylformamide is prepared under an argon atmosphere and the mixture is heated at 60° C. for 7.5 hours.

The mixture is cooled to room temperature, poured into 150 ml of water, extracted with ethyl acetate, the organic phase is washed with water, dried over magnesium sulphate, filtered and the solvent evaporated under reduced pressure. The residue is taken up with diethyl ether and 3.5 g of base are obtained.

The fumarate is prepared by addition of 1.07 g (0.009 mol) of fumaric acid, in solution in 100 ml of ethanol, to 3.45 g (0.009 mol) of base, in solution in 200 ml of ethanol. The solvent is evaporated under reduced pressure and the residue is recrystallised from 2-propanol.

2.9 g of acid fumarate are finally obtained.
Melting point: 167°-169.5° C.

EXAMPLE 4

Compound No. 10

2-[[[1-[2-(2-Methoxyphenoxy)ethyl]piperidin-3-yl]methyl]-amino]pyrimidine-4-carboxamide, fumarate.

4.1. 1,1-Dimethylethyl [[1-[2-(2-methoxyphenoxy)ethyl]-piperidin-3-yl]methyl]carbamate.

4.62 g (0.02 mol) of 2-(2-methoxyphenoxy)ethyl bromide, 4.29 g (0.02 mol) of 1,1-dimethylethyl [(piperidin-3-yl) methyl]carbamate, 3.32 g (0.024 mol) of potassium carbonate and 40 ml of N,N-dimethylformamide are introduced into a 150 ml Keller flask and the mixture is heated at between 80° and 90° C. for 6 hours under an argon atmosphere. The mixture is cooled to room temperature, poured into 500 ml of water and extracted with ethyl acetate. The organic phase is washed with water, dried over magnesium sulphate, filtered and the solvent is evaporated under reduced pressure.

The residue is taken up with petroleum ether and 6.8 g of solid are obtained which is used as it is in the following stage.

Melting point: 78°-79° C.

4.2. 1-[2-(2-Methoxyphenoxy)ethyl]piperidine-3-methenamine. 6.8 g (0.0186 mol) of 1,1-dimethylethyl [[1-[2-(2-methoxyphenoxy)ethyl]piperidin-3-yl]methyl]carbamate, 55 ml of dichloromethane and 55 ml of trifluoroacetic acid are introduced into a 250 ml round bottom flask and the mixture is heated at 40° C. for 4.5 hours.

The mixture is concentrated under reduced pressure, the crude residue is treated with 200 ml of 1N sodium hydroxide solution and the mixture is extracted with dichloromethane.

The organic phase is washed with water, dried over magnesium sulphate, filtered and the solvent evaporated under reduced pressure.

4.76 g of yellowish oil are obtained which is used as it is in the following stage.

4.3. 2-[[[1-[2-(2-Methoxyphenoxy)ethyl]piperidin-3-yl]-methyl]amino]pyrimidine-4-carboxamide, fumarate. A suspension of 4.76 g (0.018 mol) of 1-[2-(2-methoxyphenoxy)ethyl]piperidine-3-methenamine, 2.84 g (0.018 mol) of 2-chloropyrimidine-4-carboxamide, 3 g (0.0216 mol) of potassium carbonate, 0.3 g of sodium iodide and 36 ml of N,N-dimethylformamide is prepared under an argon atmosphere and the mixture is stirred at room temperature for 24 hours.

The mixture is poured into 500 ml of water, extracted with ethyl acetate, the organic phase is washed with water, dried over magnesium sulphate, filtered and the solvent evaporated under reduced pressure.

After purification of the residue by chromatography on a silica gel column (eluent: dichloromethane/ methanol 98/2 to 90/10), 4.4 g of base are finally isolated.

The fumarate is prepared by addition of 1.33 g (0.0114 mol) of fumaric acid, in solution in 100 ml of ethanol, to 4.4 g (0.0114 mol) of base, in solution in 100 ml of ethanol. The solvent is evaporated under reduced pressure and the residue is recrystallised from a mixture of 2-propanol and ethanol. 2.65 g of acid fumarate are finally obtained. Melting point: 154°-156° C.

EXAMPLE 5

Compound No. 4

2-[1-[2-[5-Methyl-2-(1-methylethyl)phenoxy]ethyl]-piperidin-4-ylamino]pyrimidine-4-carboxamide, fumarate.

5.1. 1,1-Dimethylethyl [1-[2-[5-methyl-2-(1-methylethyl)-phenoxy]ethyl]piperidin-4-yl]carbamate.

5.48 g (0.0231 mol) of 2-[5-methyl-2-(1-methyl-ethyl) phenoxy]ethyl bromide, 3.87 g (0.0193 mol) of 1,1-dimethylethyl (piperidin-4-yl)carbamate, 4.0 g (0.029 mol) of potassium carbonate and 40 ml of N,N-dimethylformamide are introduced into a 250 ml, three-necked round bottom flask and the mixture is heated at between 90° and 100° C. for 8 hours under an argon atmosphere.

The mixture is cooled to room temperature, poured into 200 ml of water and extracted with ethyl acetate. The organic phase is washed with water, dried over magnesium sulphate, filtered and the solvent evaporated under reduced pressure. The residue is purified by chromatography on a silica gel column by eluting with a 98/2 to 95/5 dichloromethane/methanol mixture. 7.1 g of amorphous solid are obtained which is used as it is in the following stage.

5.2. 1-[2-[5-Methyl-2-(1-methylethyl)phenoxy]ethyl]-piperidin-4-amine.

7.0 g (0.0186 mol) of 1,1-dimethylethyl [1-[2-[5-methyl-2-(1-methylethyl)phenoxy]-ethyl]piperidin-4-yl]carbamate, 70 ml of dichloromethane and 70 ml of trifluoroacetic acid are introduced into a 250 ml, three-necked round bottom flask and the mixture is heated at 40° C. for 4 hours.

The mixture is diluted with 150 ml of dichloromethane, cooled to 0° C., and a stream of gaseous ammonia is passed through it. The insoluble material is removed by filtration, the solvent is evaporated under reduced pressure, the residue is taken up with dichloromethane, the solution is dried over magnesium sulphate, filtered and evaporated under reduced pressure.

5.05 g of orange-coloured oil are obtained which is used as it is in the following stage.

5.3. 2-[1-[2-[5-Methyl-2-(1-methylethyl)phenoxy]ethyl]-piperidin-4-ylamino]pyrimidine-4-carboxamide, fumarate.

A suspension of 3.4 g (0.0123 mol) of 1-[2-[5-methyl-2-(1-methylethyl) phenoxy]ethyl]-piperidin-4-amine, 2.0 g (0.0127 mol) of 2-chloropyrimidine-4-carboxamide, 2.55 g (0.0185 mol) of potassium carbonate, 0.3 g of sodium iodide and 65 ml of N,N-dimethylformamide is prepared under an argon atmosphere and the mixture is heated at 60° C. for 7.5 hours.

The mixture is cooled to room temperature, poured into 150 ml of water, extracted with ethyl acetate, the organic phase is washed with water, dried over magnesium sulphate, filtered and the solvent evaporated under reduced pressure. The residue is taken up with diethyl ether, which provides 3.4 g of base which are recrystallised from toluene to give 2.6 g of white solid.

Melting point: 157.5°-160° C.

In order to prepare the fumarate from it, it is dissolved in 150 ml of ethanol and 0.76 g (0.0064 mol) of fumaric acid in solution in 100 ml of ethanol is added, the solvent is evaporated under reduced pressure and the residue is recrystallised from methanol.

3.6 g of acid fumarate are finally obtained.

Melting point: 241°-244° C.

EXAMPLE 6

Compound No. 5

2-[1-[3-(5-Fluoro-2-methoxyphenoxy)propyl]piperidin-4-ylamino]pyrimidine-4-carboxamide, fumarate.

6.1. 1,1-Dimethylethyl [1-[3-(5-fluoro-2-methoxyphenoxy)-propyl]piperidin-4-yl]carbamate.

6.35 g (0.0241 mol) of 3-(5-fluoro-2-methoxyphenoxy) propyl bromide, 4.37 g (0.0218 mol) of 1,1-dimethylethyl (piperidin-4-yl)carbamate, 4.5 g of potassium carbonate and 45 ml of N,N-dimethylformamide are introduced into a 250 ml, three-necked round bottom flask and the mixture is heated at between 90° and 100° C. for 8.5 hours under an argon atmosphere.

The mixture is cooled to room temperature, poured into 250 ml of water and extracted with ethyl acetate. The organic phase is washed with water, dried over magnesium sulphate, filtered and the solvent evaporated under reduced pressure. The residue is purified by chromatography on a silica gel column by eluting with a 97/3 to 92/8 dichloromethane/methanol mixture. 7.3 g of amorphous solid are obtained which is used as it is in the following stage.

6.2. 1-[3-(5-Fluoro-2-methoxyphenoxy)propyl]-piperidine-4-amine.

5.7 g (0.0149 mol) of 1,1-dimethylethyl [1-[3-(5-fluoro-2-methoxyphenoxy)propyl]piperidin-4-yl]-carbamate, 60 ml of dichloromethane and 60 ml of trifluoroacetic acid are introduced into a 250 ml, three-necked round bottom flask and the mixture is heated at 40° C. for 4 hours.

The mixture is diluted with 200 ml of dichloromethane, cooled to 0° C. and a stream of gaseous ammonia is passed through it. The insoluble material is removed by filtration, the solvent is evaporated under reduced pressure, the residue is taken up with dichloromethane, the solution dried over magnesium sulphate, filtered and the solvent evaporated under reduced pressure.

4.1 g of orange-coloured oil are obtained which is used as it is in the following stage.

6.3. 2-[1-[3-(5-Fluoro-2-methoxyphenoxy)propyl]-piperidin-4-ylamino]pyrimidine-4-carboxamide, fumarate.

A suspension of 3.5 g (0.0123 mol) of 1-[3-(5-fluoro-2-methoxyphenoxy) propyl]piperidin-4-amine, 2.0 g (0.0127 mol) of 2-chloropyrimidine-4-carboxamide, 2.55 g (0.0158 mol) of potassium carbonate, 0.3 g of sodium iodide and 65 ml of N,N-dimethylformamide is prepared under an argon atmosphere and the mixture is heated at 60° C. for 7 hours.

The mixture is cooled to room temperature, poured into 150 ml of water, extracted with ethyl acetate, the organic phase is washed with water, dried over magnesium sulphate, filtered and the solvent evaporated under reduced pressure. The residue is taken up with diethyl ether and 3.3 g of base are obtained which are recrystallised from toluene to give 2.55 g of solid.

The latter is dissolved in 150 ml of ethanol, 0.74 g (0.00632 mol) of fumaric acid in solution in 80 ml of ethanol are added, the solvent is evaporated under reduced pressure and the residue is recrystallised from methanol.

2.5 g of acid fumarate are finally obtained.

Melting point: 244.5°-247° C.

The following table illustrates the chemical structures and the physical properties of some compounds according to the invention.

TABLE

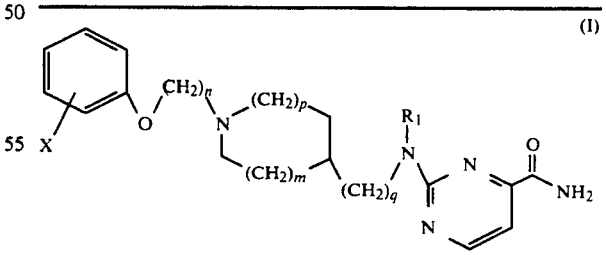

(I)

| No. | X | n | m,p | q | $R_1$ | Salt | M.p. (°C.) |
|---|---|---|---|---|---|---|---|
| 1 | 2-$OCH_3$ | 2 | 1,1 | 0 | H | HCl | 194-196 |
| 2 | 4-F | 2 | 1,1 | 0 | H | HCl | 202-205 |
| 3 | 2-$OCH_3$, 5-F | 2 | 1,1 | 0 | H | fum | 211-213.5 |
| 4 | 2-i$C_3H_7$, 5-$CH_3$ | 2 | 1,1 | 0 | H | fum | 241-244 |
| 5 | 2-$OCH_3$, 5-F | 3 | 1,1 | 0 | H | fum | 244.5-247 |
| 6 | 4-F | 3 | 1,1 | 0 | H | fum | 239-241 |
| 7 | H | 2 | 0,2 | 1 | H | fum | 167.5-170 |
| 8 | 4-F | 2 | 1,1 | 1 | H | fum | 167-169.5 |
| 9 | 4-F | 2 | 0,2 | 1 | H | $\frac{2}{3}$ fum | 170-173 |

TABLE-continued (I)

| No. | X | n | m,p | q | R₁ | Salt | M.p. (°C.) |
|---|---|---|---|---|---|---|---|
| 10 | 2-OCH₃ | 2 | 0,2 | 1 | H | fum | 154–156 |
| 11 | 2-OCH₃, 5-Cl | 2 | 1,1 | 1 | H | fum | 172.5–175 |

Note: in column "X", "iC₃H₇" denotes a 1-methylethyl group; in column "Salt", "HCl" denotes a hydrochloride, "fum." denotes a hydrogen fumarate (1 mole of base per 1 mole of diacid) and "⅔fum." denotes a fumarate composed of 2 moles of base and 3 moles of diacid.

The compounds of the invention were made the subject of studies regarding their antagonist activity of $\alpha_1$-adrenergic receptors at the level of the lower urinary apparatus.

Their in vitro activity was studied on isolated rabbit urethra.

Adult rabbit urethra rings are prepared according to the method of Ueda et al., Eur. J. Pharmacol., (1984), 103, 249–254, and then, after sensitisation to noradrenalin, the concentration-response curve to phenylephrine is determined in the absence and in the presence of the study compound.

The potency of the $\alpha_1$-adrenergic antagonism of each compound is evaluated by calculation of the pA₂, the antilogarithm of the molar concentration of the antagonist in the presence of which the concentration of the agonist must be doubled to cause the same effect as in its absence.

The pA₂ values of the compounds are of the order of 5.5 to 9.

The in vivo activity of the compounds of the invention was studied with regard to their effect on the urethral hypertonia caused by the stimulation of the sympathetic fibres of the hypogastric nerve in anaesthetized cat.

Adult male cats are anaesthetized by sodium pentobarbital and they are prepared according to the method of Theobald, J. Auton. Pharmac. (1983), 3, 235–239, in order to obtain a urethral hypertonia by stimulation of the sympathetic fibres of the hypogastric nerve. The contractile responses of the urethra to the electrical stimulation of the hypogastric nerve are recorded before and after intravenous administration of the study compounds, at cumulative doses from 1 to 1000 μg/kg.

The strength of the $\alpha_1$-adrenergic antagonism of each compound is evaluated by calculation of the ID₅₀, the dose which inhibits by 50% the urethral hypertonia.

The ID₅₀ values of the compounds of the invention are of the order of 0.01 to 1 mg/kg.

The results of the tests show that the compounds of the invention show, in vitro, an antagonist activity of the $\alpha_1$-adrenergic receptors of the smooth muscles of the lower urinary apparatus (urethra) stimulated by an $\alpha_1$-adrenergic agonist (phenylephrine). In vivo, they inhibit the urethral hypertonia caused by sympathetic nervous stimulation.

The invention therefore includes a method of treatment of disorders involving $\alpha_1$-adrenergic receptors, which comprises administering to a patient a compound of the invention.

The compounds of the invention can thus be used for the symptomatic treatment of diseases and complaints which involve a hyperactivity of the $\alpha$-adrenergic system at the level of the lower urinary apparatus, and especially for the treatment of benign hypertrophia of the prostate, of dysuria and of pollakiuria.

The invention includes pharmaceutical compositions comprising a compound of the invention and a pharmaceutically acceptable carrier or diluent.

Compounds of the invention can be introduced in all forms appropriate for enteral or parenteral administration, combined with pharmaceutical excipients, for example in the form of tablets, sugar- coated pills, gelatin capsules, capsules, drinkable or injectable solutions or suspensions, or suppositories, the charges being such as to allow a daily dose from 0.5 to 500 mg of active substance.

We claim:

1. A compound which is a 2-aminopyrimidine carboxamide derivative represented by formula (I)

(I)

in which
X represents one or more substituents which may be the same or different when more than one substituent is present selected from the group consisting of hydrogen, fluorine, chlorine, methyl, 1-methylethyl and methoxy,
n represents 2 or 3,
m represents 1, in which case p represents 1, or
m represents 0, in which case p represents 2,
q represents 0 or 1, and
R₁ represents a hydrogen atom;
or a pharmaceutically acceptable acid addition salt thereof.

2. A compound according to claim 1 wherein m is 0 and p is 2, and which is a pure enantiomer or a mixture of enantiomers.

3. A compound according to claim 1 wherein one or two substituents X are present.

4. A compound according to claim 3 wherein one substituent X is present and which is at the 2- or 4-position.

5. A compound according to claim 3 wherein two substituents X are present at the 2- and 5-positions.

6. A pharmaceutical composition comprising an effective amount of a compound as claimed in claim 1 for treating disorders involving hyperactivity of the $\alpha$-adrenergic system in the lower urinary system and a pharmaceutically acceptable carrier or diluent.

7. A method of treatment of disorders involving hyperactivity of the $\alpha$-adrenergic system in the lower urinary system which comprises administering to a patient an effective amount of a compound as claimed in claim 1.

* * * * *